United States Patent [19]

Porteous

[11] Patent Number: 4,930,660
[45] Date of Patent: Jun. 5, 1990

[54] COMBINATION WORKING TRAY AND STERILIZATION CASE FOR MEDICAL INSTRUMENTS

[76] Inventor: Don D. Porteous, 2794 Moraga Dr., Los Angeles, Calif. 90024

[21] Appl. No.: 319,279

[22] Filed: Mar. 6, 1989

[51] Int. Cl.⁵ .............................................. B65D 1/36
[52] U.S. Cl. .................................... 220/367; 206/63.5
[58] Field of Search ............... 220/4 E, 367; 206/63.5, 206/439, 443

[56] References Cited

U.S. PATENT DOCUMENTS

| | | | |
|---|---|---|---|
| 3,285,409 | 11/1966 | Loran | 206/63.5 |
| 4,353,694 | 10/1982 | Pelerin | 206/63.5 X |
| 4,576,307 | 3/1986 | Frydenberg | 220/4 E X |
| 4,671,943 | 6/1987 | Wahlquist | 206/439 X |
| 4,798,292 | 1/1989 | Hauze | 220/367 X |

Primary Examiner—Steven M. Pollard
Attorney, Agent, or Firm—Donald Diamond

[57] ABSTRACT

A combination working tray and sterilization case is provided for medical instruments, wherein first and second ventilated shell halves are pivotally connected to each other for movement between open and closed positions, thereby forming a tray in the open position and a sterilization case in the closed position. A spring is provided in each of the first and second shell halves in order to hold medical instruments between adjacent convolutions of each spring.

10 Claims, 2 Drawing Sheets

COMBINATION WORKING TRAY AND STERILIZATION CASE FOR MEDICAL INSTRUMENTS

BACKGROUND OF THE INVENTION

1. Field of the Invention

The present invention relates generally to containers having multiple uses and, more particularly, to a combination working tray and sterilization case for medical instruments.

2. Description of the Related Art

In the field of dentistry, it is common practice for a dentist to use multiple hand-held instruments when working in a patient's mouth. Generally, these instruments have elongated cylindrical bodies with opposite ends shaped to provide a particular function.

When a dentist uses the various instruments, a tray is required to organize and hold the instruments. Trays in common usage today simply provide a planar support surface upon which the instruments rest. Thus, unless the tray is resting on a perfectly level surface, the instruments tend to move under the influence of gravity, and generally tend towards disorganization.

After using the instruments on one patient, the dentist is required to sterilize the instruments prior to using them on the next patient. Typically, steam sterilizers expose the instruments to high temperature steam, thereby effecting sterilization. However, if the instruments are handled to remove them from the steam sterilizer, the sterilized condition will be lost.

SUMMARY OF THE INVENTION

An object of the present invention is to provide a single apparatus operable in a first mode as a working tray and in a second mode as a sterilization case for medical instruments, particularly dental instruments.

Another object of the invention is to provide a sterilization case capable of being placed in a steam sterilizer without directly handling the instruments contained in the sterilization case, thereby preventing contamination after sterilization.

Another object of the invention is to provide a combination working tray and sterilization case which can quickly and easily be converted from one mode of operation to another, due to a relatively simple construction.

Another object of the invention is to provide a tray capable of organizing dental instruments during usage, and being further capable of carrying or storing dental instruments when not in use.

In accordance with a preferred embodiment of the present invention, a combination working tray and sterilization case for medical instruments includes first and second ventilated shell halves pivotally connected to each other for movement between open and closed positions, thereby forming a tray in the open position and a sterilization case in the closed position, and means disposed in at least one of the shell halves for releasably holding medical instruments. Preferably, the holding means comprises a coil spring having a plurality of spaced apart convolutions and being mounted transversely in one or both of the first and second shell halves, such that any two adjacent convolutions are operable to frictionally engage a medical instrument therebetween.

The coil spring is capable of holding a plurality of medical instruments within the two shell halves without actually touching any of the surfaces thereof. This feature facilitates a more complete exposure of the surfaces of each medical instrument to the sterilizing steam.

These objects, together with other objects and advantages which will be subsequently apparent reside in the details of construction and operation of the combination working tray and sterilization case as more fully hereinafter described and claimed, reference being had to the accompanying drawings forming a part hereof, wherein like reference numerals refer to like parts throughout.

DETAILED DESCRIPTION OF THE PREFERRED EMBODIMENTS

Figure 1:
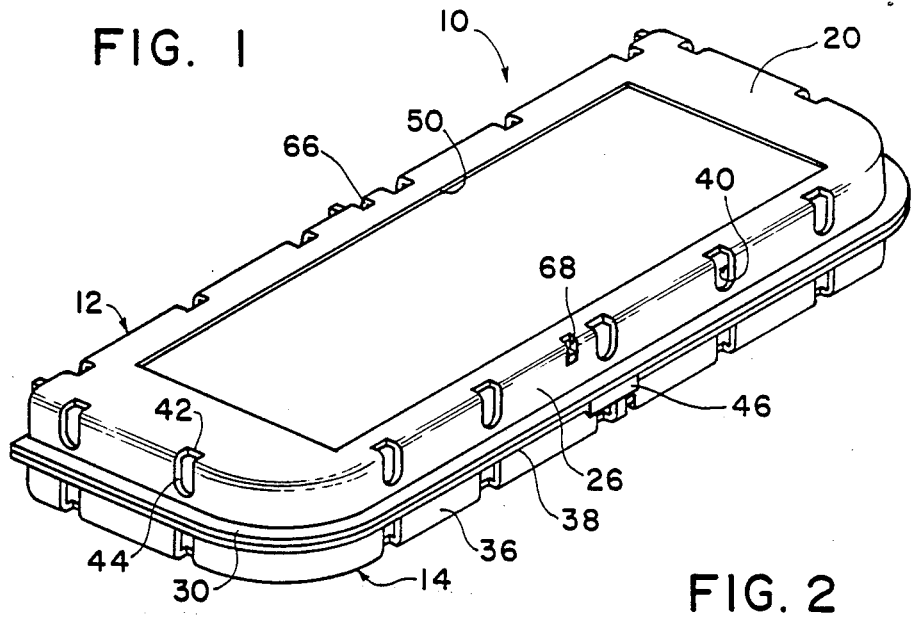
FIG. 1 is a perspective view of a first preferred embodiment of the present invention.
Figure 2:
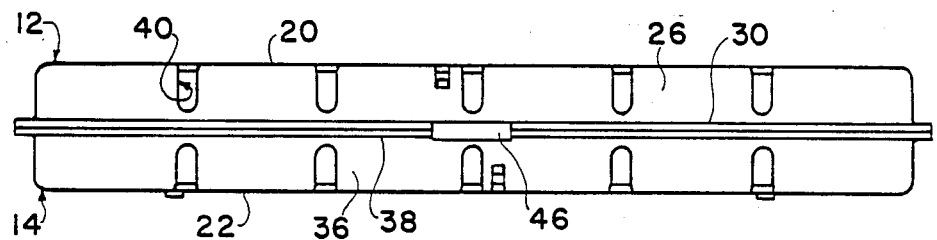
FIG. 2 is a side elevational view of the embodiment of FIG. 1.
Figure 3:
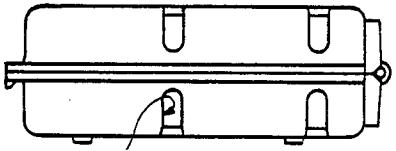
FIG. 3 is a rear view of the embodiment of FIG. 1.
Figure 4:
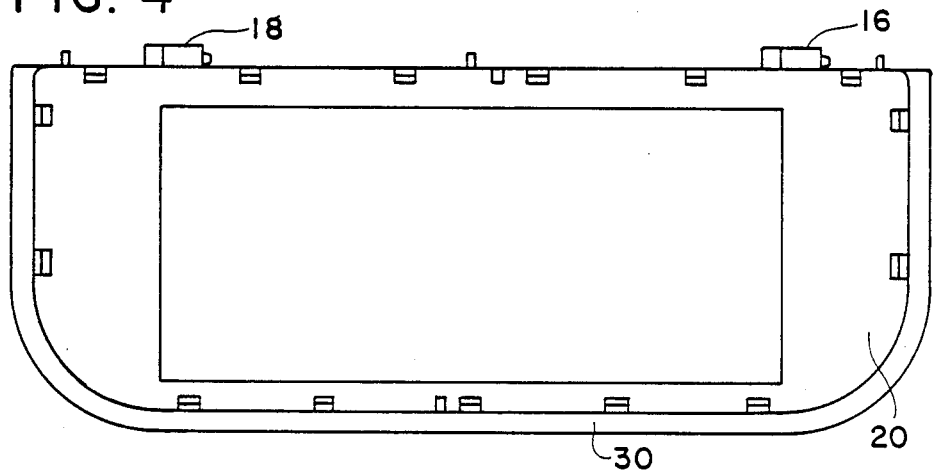
FIG. 4 is a top view of the embodiment of FIG. 1.
Figure 5:
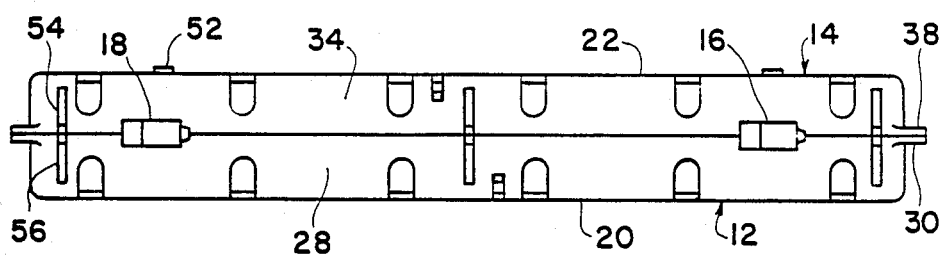
FIG. 5 is an opposite side elevational view of the embodiment of FIG. 1.
Figure 6:
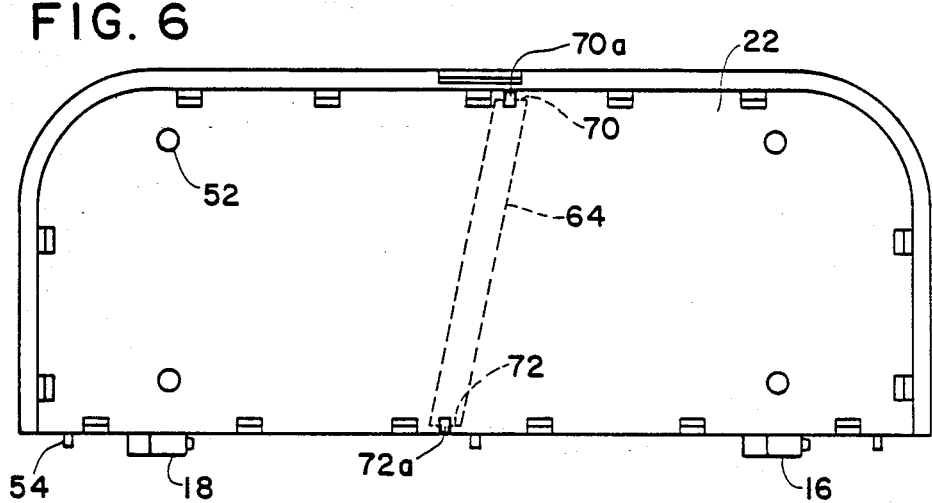
FIG. 6 is a bottom view of the embodiment of FIG. 1.

Referring to FIGS. 1-7, a combination working tray and sterilization case for medical instruments is generally referred to by the numeral 10. The device is illustrated as a sterilization case in FIG. 1 and includes a first shell half 12 and a second shell half 14, the two halves being pivotally connected to each other for movement between open and closed positions by means of hinges 16 and 18.

Each of the first and second shell halves 12 and 14 has a planar portion 20 and 22, respectively. A sidewall portion 24 of shell half 12 extends upwardly from the planar portion 20 along a peripheral edge thereof. The sidewall portion 24 includes parallel opposite sidewalls 26 and 28 which extend in the longitudinal direction of the shell half 12. A flange 30 is formed at the upper end of the sidewall portion 24 except at sidewall 28 which is left unflanged in order to facilitate relative pivotal movement between the two shell halves 12 and 14 by means of the hinges 16 and 18.

Shell half 14 is symmetric with and the mirror-image of shell half 12. Thus, shell half 14 includes a sidewall portion 32 which extends upwardly from a peripheral edge of the planar portion 22. The sidewall portion 32 includes parallel sidewalls 34 and 36 which are disposed in a longitudinal direction of shell half 14. A flange 38 is formed at the upper end of the sidewall portion 32 except along sidewall 34, so as to facilitate pivotal movement of the two halves relative to each other by means of the hinges 16 and 18.

The two shell halves are ventilated by means of a plurality of apertures 40, each having a first portion 42 formed in the planar portions 20 and 22 of the two shell halves 12 and 14, and a second portion 44 formed in the sidewall portions 24 and 32 of the two shell halves. The second portion 44 of the apertures 40 proVides steam condensate drainage from within the sterilization case. Also, when the device is in the working tray mode illustrated in FIG. 7, the first portions 42 of the apertures 40 can provide liquid drainage if necessary.

Preferably, the two shell halves 12 and 14 are each molded in one piece from heat resistant plastic. One-piece molding allows for a latch 46 to be integrally formed on the flange 30 of the shell half 12. The latch 46, since it is made of plastic material, resiliently springs into a catch 48 integrally formed in the flange 38 of the shell half 14. To release the latch and thus open the sterilization case, the latch may be pulled outwardly away from the catch, or vice versa.

In addition to the integrally formed latch and catch, a slightly recessed area 50 may be provided in the planar portion 20 of the shell half 12, while support legs 52 may be provided on the opposite shell half 14 extending downwardly from the planar portion 22. The legs are for resting the device in a steam sterilizer.

In addition, the shell halves may be provided with abutments 54 and 56 which are integrally formed on the sidewalls 34 and 28, respectively, so that when the two shell halves are pivoted to the working tray mode of operation, the abutments become juxtaposed to abut each other and support the device in a substantially flat, tray-like disposition.

Figure 7:
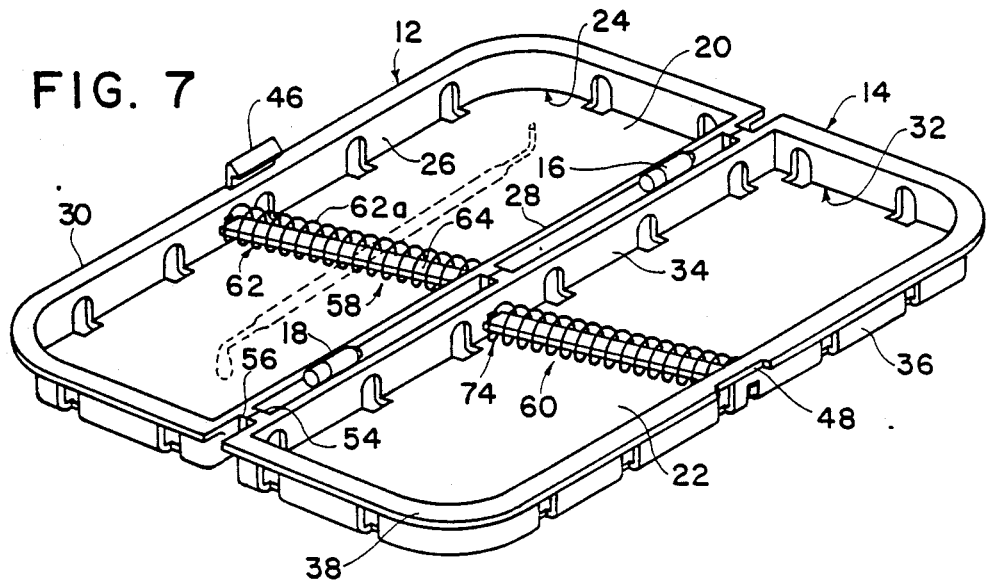
FIG. 7 is a perspective view of the embodiment of FIG. 1 after conversion from the sterilization case mode of operation to the working tray mode of operation.

Referring to FIG. 7, first and second holding means are generally referred to by the numerals 58 and 60. The holding means are essentially resilient holders disposed in the first and second shell halves 12 and 14, respectively. Holding means 58 includes a coil spring 62 which is preferably slightly compressed between the opposite sidewalls 26 and 28. While abutting the opposite sidewalls 26 and 28 at the opposite ends thereof, the coil spring 62 is not directly connected to the sidewalls. Instead, a rhomboid bar 64 passes through the coil spring 62 and is snap fitted at its opposite ends into holes 66 and 68 provided in the opposite sidewalls 26 and 28 of the first shell half 12. As shown in FIG. 1, the holes 66 and 68 are staggered along the length of the shell half 12 so that the short, angled surfaces 70 and 72 of the rhomboid bar 64 (FIG. 6), which are parallel to each other and angled relative to the longer parallel surface, are parallel to the opposite sidewalls 26 and 28. The rhomboid bar 64 snaps into the holes by means of pins 70a and 72a provided on opposite ends of the bar 64. Again, since the shell halves are made of plastic, the bar 64 can be removed by pushing the sidewalls 26 and 28 apart.

The coil spring 62 includes a plurality of convolutions 62a which are spaced apart such that any two adjacent convolutions are operable to frictionally engage a medical instrument (shown in broken lines in FIG. 7) therebetween. By mounting the bar 64 obliquely relative to and between the sidewalls, the convolutions become parallel to the opposite sidewalls. In other words, if the coil spring ran perpendicularly between the opposite sidewalls, any medical instruments held between adjacent convolutions would be mounted at an angle relative to the parallel sidewalls 26 and 28 due to the pitch or spiral of the coil. This would be somewhat inconvenient since the device of the present invention is intended to handle elongated instruments. Therefore, one of the many salient features of the present invention is that by obliquely mounting the bar 64, the spiral in the coil spring is compensated for so as to orient the convolutions parallel to the sidewalls.

An identical coil spring 74 is provided for the holding means 60 in the second shell half 14.

When instruments are held between adjacent convolutions of either coil spring 62 or 74, or both, the instruments will be held by the spring without touching any of the surfaces of either shell half 12 or 14. Thus, a more complete sterilization can occur by maximizing the exposure of surfaces of the instruments to the sterilizing steam.

The many features and advantages of the present invention are apparent from the detailed specification, and thus, it is intended by the appended claims to cover all such features and advantages of the combination working tray and sterilization case which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and spirit of the invention.

What is claimed is:

1. A combination working tray and sterilization case for medical instruments comprising:
    first and second ventilated shell halves pivotally connected to each other for movement between open and closed positions, thereby forming a tray in the open position and a sterilization case in the closed position, wherein each of the first and second shell halves comprises a planar portion and a sidewall portion including two parallel, longitudinally extending, opposite sidewalls; and
    holding means for releasably holding medical instruments, said holding means comprising a first coil spring disposed in the first shell half and having a plurality of spaced apart convolutions with any two adjacent convolutions being operable to frictionally engage a medical instrument, said first coil spring being mounted obliquely relative to the opposite sidewalls of the first shell half at an angle sufficient to orient the convolutions parallel to the opposite sidewalls, and said holding means further comprising a first rhomboid bar extending between the opposite sidewalls of the first shell half and through said first coil spring.

2. A combination working tray and sterilization case as claimed in claim 1, wherein the holding means comprises a second coil spring disposed in the second shell half and having a plurality of spaced apart convolutions with any 2 adjacent convolutions being operable to frictionally engage a medical instrument, said second coil spring being mounted obliquely relative to the opposite sidewalls of the second shell half at an angle sufficient to orient the convolutions parallel to the opposite sidewalls, and further comprises a second rhomboid bar extending between the opposite sidewalls of the second shell half and through the second coil spring.

3. A combination working tray and sterilization case as claimed in claim 2, wherein the first and second rhomboid bars have two parallel long surfaces and two parallel short surfaces angled relative to the long surface, the short angled surfaces being lockable into an abutting position with the opposite sidewalls of the respective first and second shell halves by locking means.

4. A combination working tray and sterilization case as claimed in claim 3, wherein the locking means comprises a pin extending outwardly from each angled surface of the first and second rhomboid bars and a pair of staggered holes, one provided in each opposite sidewall of the respective first and second shell halves.

5. A combination working tray and sterilization case as claimed in claim 1, further comprising hinges for pivotally connecting the first and second shell halves and being disposed on a first of the two opposite sidewalls of the first and second shell halves.

6. A combination working tray and sterilization case as claimed in claim 5, further comprising a latch for releasably holding the first and second shell halves in the closed position and being disposed on a second of the two opposite sidewalls of the first and second shell halves.

7. A combination working tray and sterilization case as claimed in claim 5, further comprising abutments formed on at least one of the first and second shell halves and being operative to maintain a flat, side-by-side disposition of the first and second shell halves when in the open position.

8. A combination working tray and sterilization case as claimed in claim 1, wherein the first and second shell halves are each one-piece molded of heat resistant plastic material.

9. A combination working tray and sterilization case as claimed in claim 1, wherein the first and second shell halves include a plurality of apertures providing steam passages.

10. A combination working tray and sterilization case as claimed in claim 1, wherein the first and second shell halves include a plurality of apertures providing steam passages, each aperture having a first portion formed in the planar portion and a second portion formed in the sidewall portion of the first and second shell halves, the second portion of the aperture providing steam condensate drainage.

* * * * *